United States Patent
Nikiforov et al.

(10) Patent No.: US 11,891,667 B2
(45) Date of Patent: *Feb. 6, 2024

(54) IGF2BP3 FUNCTIONAL ALTERATIONS AND OVEREXPRESSION AS A MARKER FOR CANCER DIAGNOSIS AND THERAPEUTIC RESPONSE TO IGF1R INHIBITORS

(71) Applicants: UNIVERSITY OF PITTSBURGH-OF THE COMMONWEALTH SYSTEM OF HIGHER EDUCATION, Pittsburgh, PA (US); Yuri E. Nikiforov, Pittsburgh, PA (US)

(72) Inventors: Yuri E. Nikiforov, Pittsburgh, PA (US); Marina N. Nikiforova, Pittsburgh, PA (US)

(73) Assignees: Yuri Nikiforov, Pittsburgh, PA (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/346,540

(22) Filed: Jun. 14, 2021

(65) Prior Publication Data

US 2022/0033914 A1 Feb. 3, 2022

Related U.S. Application Data

(63) Continuation of application No. 15/455,705, filed on Mar. 10, 2017, now Pat. No. 11,035,007.

(60) Provisional application No. 62/307,041, filed on Mar. 11, 2016.

(51) Int. Cl.
*C12Q 1/6886* (2018.01)

(52) U.S. Cl.
CPC ...... *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 11,035,007 B2 * 6/2021 Nikiforov .............. A61K 45/06

OTHER PUBLICATIONS

Rippe et al Oncogene. 2003. 22: 6111-6114 (Year: 2003).*
Nikiforov et al Cancer. 2014. 120: 3627-3634 (Year: 2014).*
Jin et al Diagn Mol Pathol. 2010. 19: 63-69 (Year: 2010).*
Panebianco et al PNAS. Feb. 28, 2017. 114(9): 2307-2312 (Year: 2017).*

* cited by examiner

*Primary Examiner* — Carla J Myers
(74) *Attorney, Agent, or Firm* — Meunier Carlin & Curfman LLC

(57) ABSTRACT

The present disclosure provides systems and methods for the highly sensitive and effective treatment and diagnosis of cancer. The methods disclosed herein take advantage of the discovery of a series of newly identified, inter-chromosomal genetic fusion events that occur upstream from the IGF2BP3 gene, which result in elevated expression of IGF2BP3 protein. The present disclosure utilizes biomarkers developed using this set of newly discovered genetic fusion events and elevated expression of IGF2BP3 protein to not only diagnosis cancer with high sensitivity and reliability, but also to pre-select patient populations that are expected to display an elevated likelihood of success when treated with any of numerous inhibitors of IGF1R-mediated signaling.

10 Claims, 10 Drawing Sheets

Specification includes a Sequence Listing.

Figures 2A & B
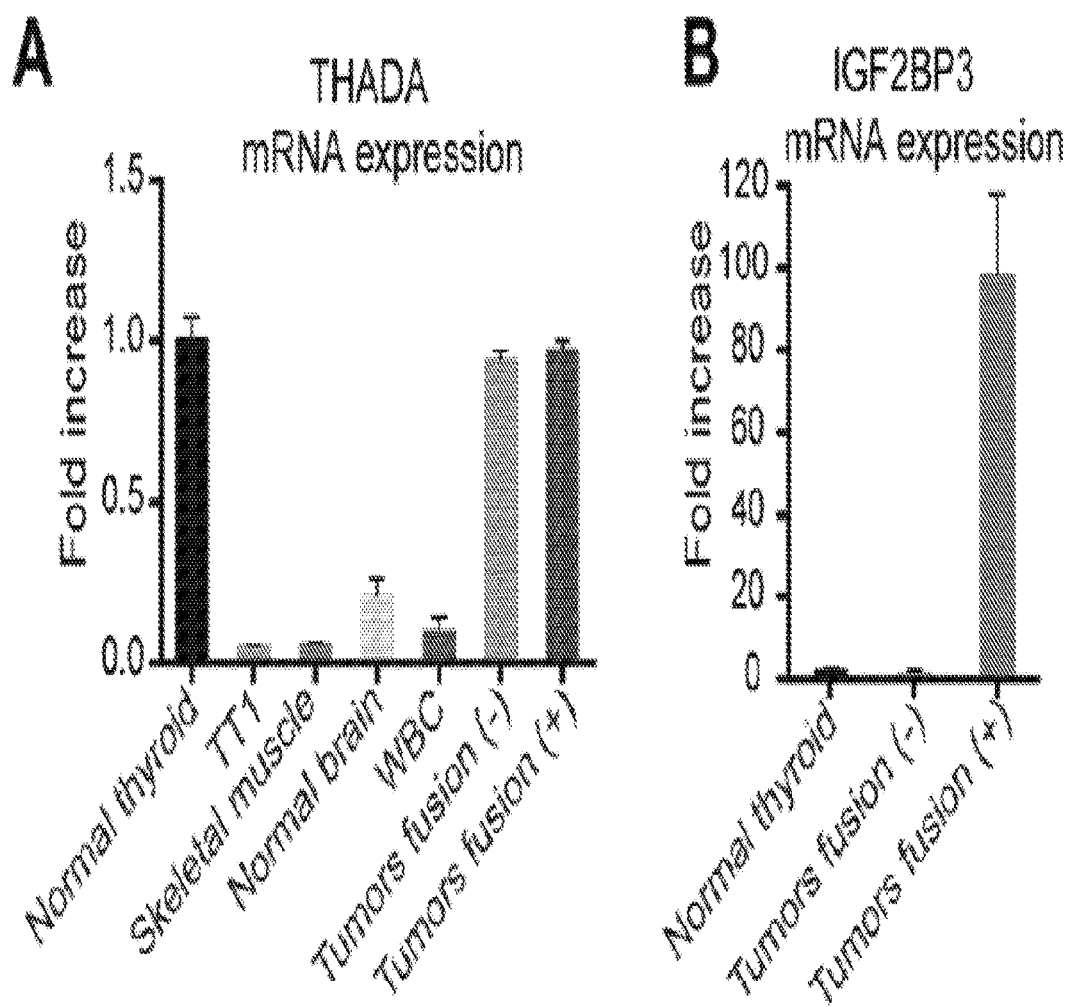

Figures 3A-D
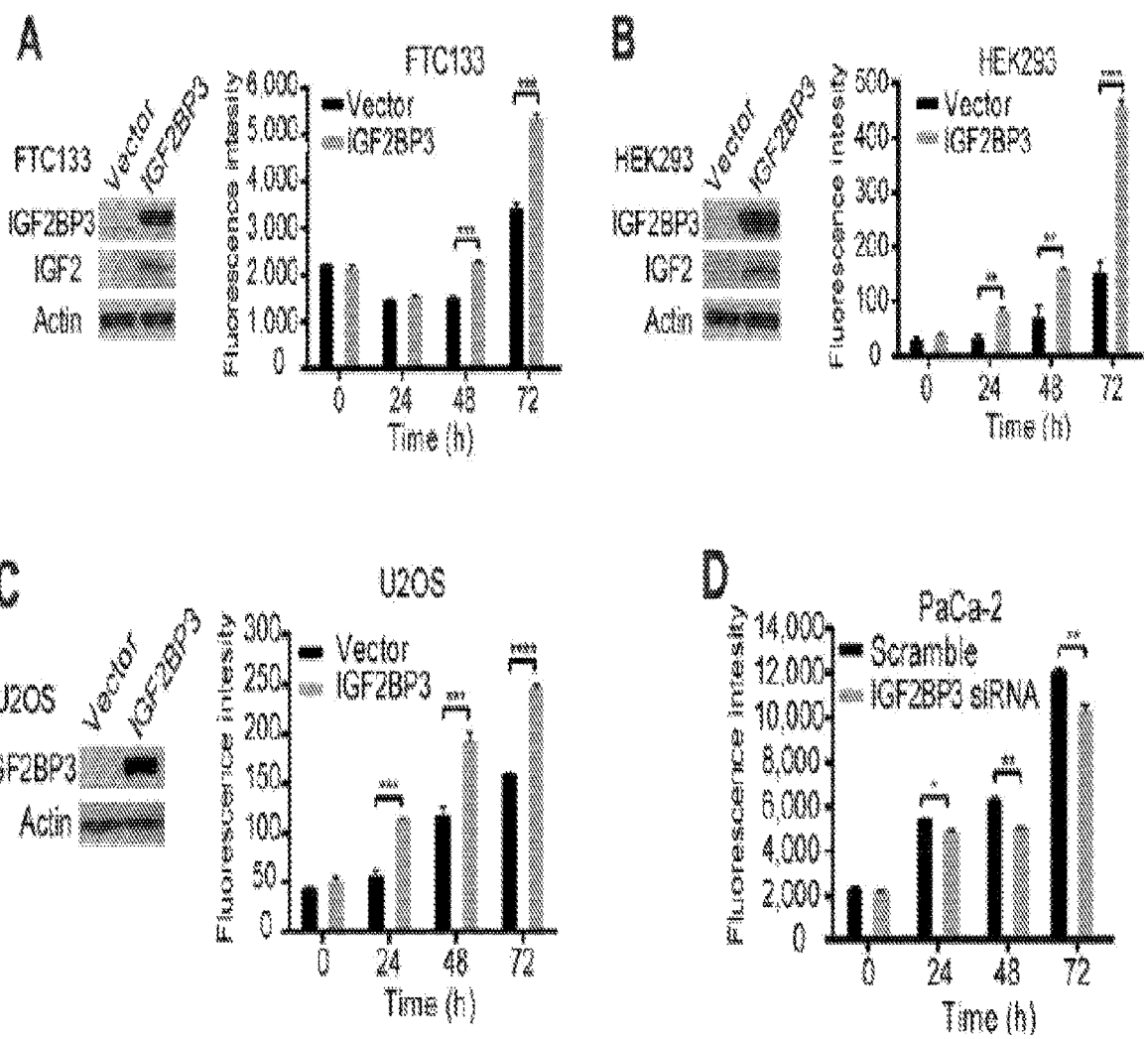

Figures 5A-C
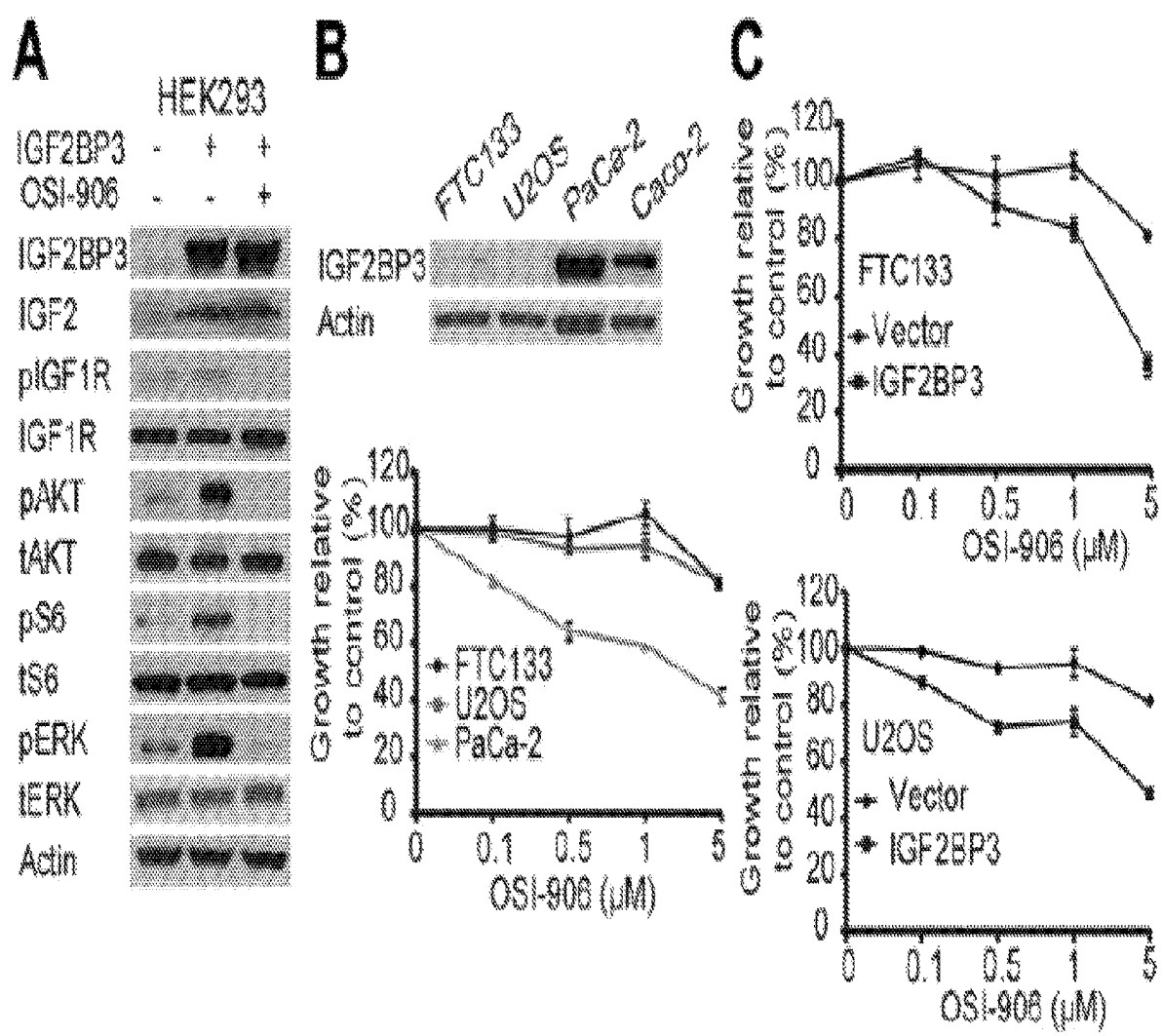

Figures 5 D-G
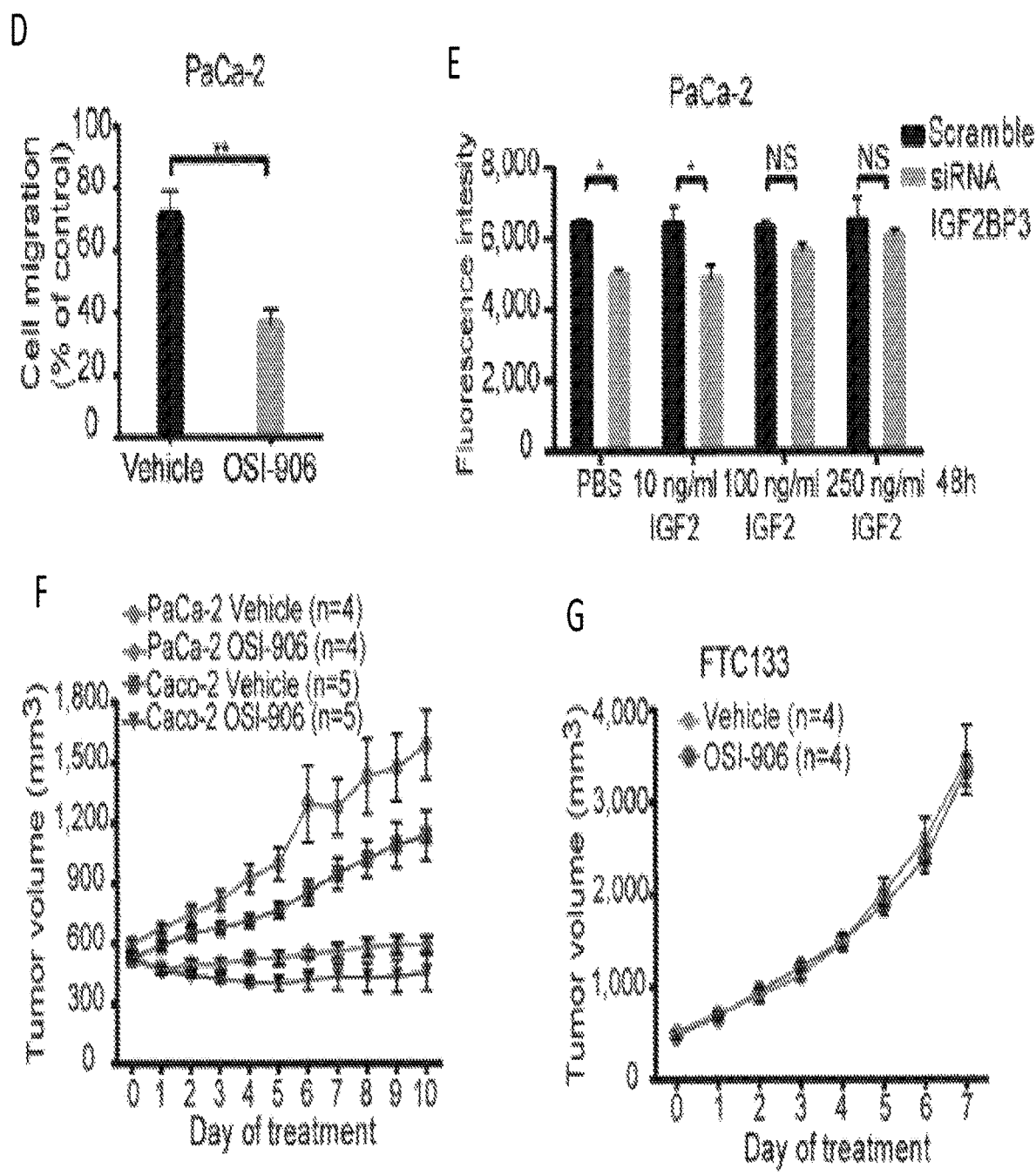

SEQUENCE LISTING

```
<160> NUMBER OF SEQ ID NOS: 17

<210> SEQ ID NO 1
<211> LENGTH: 20
<212> TYPE: DNA
<213> ORGANISM: Homo sapiens

<400> SEQUENCE: 1
atgggagaac caaatcgtca                                               20

<210> SEQ ID NO 2
<211> LENGTH: 20
<212> TYPE: DNA
<213> ORGANISM: Homo sapiens

<400> SEQUENCE: 2
tgtctaccac tcccgtgaaa                                               20
```

```
<210> SEQ ID NO 3
<211> LENGTH: 21
<212> TYPE: DNA
<213> ORGANISM: Homo sapiens

<400> SEQUENCE: 3
ctcagactcc aaacacggaa c                                             21

<210> SEQ ID NO 4
<211> LENGTH: 22
<212> TYPE: DNA
<213> ORGANISM: Homo sapiens

<400> SEQUENCE: 4
ttgcaggata cacttgctct ct                                            22

<210> SEQ ID NO 5
<211> LENGTH: 20
<212> TYPE: DNA
<213> ORGANISM: Homo sapiens

<400> SEQUENCE: 5
gctcccaacg aaatggataa                                               20

<210> SEQ ID NO 6
<211> LENGTH: 20
<212> TYPE: DNA
<213> ORGANISM: Homo sapiens

<400> SEQUENCE: 6
ccaaaggaat gaggctgaat                                               20

<210> SEQ ID NO 7
<211> LENGTH: 27
<212> TYPE: DNA
<213> ORGANISM: Homo sapiens

<400> SEQUENCE: 7
ttttctacca gtaagagtac caagtca                                       27

<210> SEQ ID NO 8
<211> LENGTH: 20
<212> TYPE: DNA
<213> ORGANISM: Homo sapiens

<400> SEQUENCE: 8
atacggaaac gaaggcagtg                                               20

<210> SEQ ID NO 9
<211> LENGTH: 21
<212> TYPE: DNA
<213> ORGANISM: Homo sapiens

<400> SEQUENCE: 9
tgcttgtgca tttgatttca t                                             21

<210> SEQ ID NO 10
<211> LENGTH: 20
<212> TYPE: DNA
<213> ORGANISM: Homo sapiens

<400> SEQUENCE: 10
```

```
aagggaatcc cgttatcagc                                                    20

<210> SEQ ID NO 11
<211> LENGTH: 21
<212> TYPE: DNA
<213> ORGANISM: Homo sapiens

<400> SEQUENCE: 11
ctcagactcc aaacacggaa c                                                  21

<210> SEQ ID NO 12
<211> LENGTH: 20
<212> TYPE: DNA
<213> ORGANISM: Homo sapiens

<400> SEQUENCE: 12
gcaaaatcca tgtttggtga                                                    20

<210> SEQ ID NO 13
<211> LENGTH: 26
<212> TYPE: DNA
<213> ORGANISM: Homo sapiens

<400> SEQUENCE: 13
cgatcacctt ctccttatta tagtcg                                             26

<210> SEQ ID NO 14
<211> LENGTH: 22
<212> TYPE: DNA
<213> ORGANISM: Homo sapiens

<400> SEQUENCE: 14
ttgcaggata cacttgctct ct                                                 22

<210> SEQ ID NO 15
<211> LENGTH: 20
<212> TYPE: DNA
<213> ORGANISM: Homo sapiens

<400> SEQUENCE: 15
aacgcgtagc cagtcttcac                                                    20

<210> SEQ ID NO 16
<211> LENGTH: 20
<212> TYPE: DNA
<213> ORGANISM: Homo sapiens

<400> SEQUENCE: 16
ggaccgagtg ctcaacttct                                                    20

<210> SEQ ID NO 17
<211> LENGTH: 20
<212> TYPE: DNA
<213> ORGANISM: Homo sapiens

<400> SEQUENCE: 17
acagctctcc accactccat                                                    20
```

IGF2BP3 FUNCTIONAL ALTERATIONS AND OVEREXPRESSION AS A MARKER FOR CANCER DIAGNOSIS AND THERAPEUTIC RESPONSE TO IGF1R INHIBITORS

CROSS-REFERENCE TO RELATED APPLICATIONS

This application is a continuation of U.S. patent application Ser. No. 15/455,705, filed Mar. 10, 2017, which claims the benefit under 35 U.S.C. § 119(e) of the earlier filing date of U.S. Provisional Patent Application No. 62/307,041 filed on Mar. 11, 2016.

STATEMENT OF GOVERNMENT SUPPORT

This invention was made with government support under CA088041 awarded by the National Institutes of Health. The government has certain rights in the invention.

BACKGROUND OF THE INVENTION

1. Field of the Invention

The present invention relates generally to the field of cellular and molecular biology, and more specifically to providing effective diagnostic tools and treatments for various types of cancer.

2. Description of the Background

While it is known that numerous cancers are caused by genetic and biochemical dysregulation, pharmacological and immunological tools that impact those biochemical systems have inconsistent effects on the growth of tumor cells. For example, over-activation of insulin-like growth factor receptor 1 (IGF1R) has been implicated in thyroid and other highly aggressive cancer types. Nevertheless, potent inhibitors of IGF1R signaling and activation (e.g., linsitinib, monoclonal antibodies to IGF) have been ineffective in the vast majority of patients in clinical trials. While it is generally thought that diversity amongst the underlying etiology may cause variable responsiveness to IGF1R signaling inhibitors, no specific basis for the heterogeneity has been identified.

Numerous small molecule inhibitors of IGF1R signaling and monoclonal antibodies targeted to IGF1R signaling have been developed and clinically evaluated as possible chemotherapeutic agents in the treatment of cancers. For example, monoclonal antibodies targeted to the IGF1R/IGF2R receptors and the IGF ligand have been employed in phase I, II, and III clinical studies for the treatment of breast, colorectal, head and neck, liver, neuroendocrine, esophageal, prostate, sarcoma, soft tissue sarcoma, and non-small cell lung cancer. Similarly, small molecule inhibitors of IGF1R signaling (e.g., linsitinib, XL228, AXL1717, and INSM-18) have been tested in phase I, II, and III clinical trials for the treatment of solid tumors, breast cancer, liver cancer, non-small cell lung cancer, ovarian cancer, and adrenocortical carcinomas. See, e.g., Scagliotti G V & Novello S, "The Role of the Insulin-like Growth Factor Signaling Pathway in Non-small Cell Lung Cancer and other Solid Tumors" *Cancer Treat. Rev.* 2012 38(4):292-302 (Tables 1 and 2). The efficacy of those therapeutic agents has been variable with many studies being discontinued because of inconsistent therapeutic impact. Specifically, linsitinib (a high-affinity antagonist of IGF1R tyrosine kinase activity) was investigated for treatment of colorectal cancer, non-small cell lung cancer, sarcoma, and other cancer types in which IGF1R signaling has been implicated, but only low levels of tumor responsiveness were observed. See Jams S T & Lovly C M, "Molecular Pathways: Clinical Applications and Future Direction of Insulin-like Growth Factor-1 Receptor Pathway Blockade" *Clin. Cancer Res.* 2015; 21(19): 4270-7 (Table 1). Indeed, numerous phase trials utilize these therapeutic agents have been discontinued due to low response rate. See Chen & Sharon, "IGF-1R as an anti-cancer target-trials and tribulations" *Chinese J Cancer,* 2013 32(5): 242-52; King H et al., "Can we unlock the potential of IGF-1R inhibition in cancer therapy?" *Cancer Treat Rev* 2014; 40(9):1096-1105. Researchers have suggested that identifying patient selection markers (to identify more responsive patient populations) is a critical step for future IGF1R inhibitor development. See Chen & Sharon at 249; King et al., Tables 1-2. Nonetheless, no predictive markers for IGF1R inhibitors are currently available. Id.

The complex genetic and biochemical regulation of IGF1R signaling cascades may provide a possible basis for the observed variable responsiveness of patients to small-molecule inhibitors. IGR1R is a member of the insulin receptor tyrosine kinase family of signaling molecules, which also includes IGF2R and the insulin receptor. IGF1R may form a homodimer receptor in vivo that can be activated by the peptide ligands insulin-like growth factor-1 (IGF1) and insulin-like growth factor (IGF2). Once activated, IGF1R activates numerous downstream pathways within the cell, including the PI3K-AKT1-mTOR pathway and the MAPK pathway—both of which have been implicated in tumorigenesis and tumor growth for numerous cancer types, including breast cancer, sarcoma, and thyroid papillary thyroid cancer, among others. Activation of IGF1R has been shown to play a major role in anchorage-independent growth of tumor cells.

The biochemical cascades triggered by IGF1R activation are tightly regulated by biochemical and genetic mechanisms. At one level, regulation of IGF1R signaling is achieved through control of ligand availability by numerous IGF-binding proteins, including IGFBP-1 through -6. Those serum-based proteins bind to the IGF ligands, thus preventing their activation of IGF1R.

IGF ligand production is further regulated through genetic mechanisms. For example, the expression of IGF2 protein is regulated by IGF2 mRNA-binding proteins (IGF2BP1 through -3), which bind to mRNA encoding IGF2 and control its stability and translation. Bell J L et al. "Insulin-like growth factor 2 mRNA-binding proteins (IGF2BPs): post-transcriptional drives of cancer progression?" *Cell Mol Life Sci* 2013; 70: 2657-75. In particular, IGF2BP3 binds to IGF2 mRNA and serves as an activator of IGF2 translation. Thus, higher levels of IGF2BP3 result in increased IGF2 translation, and subsequent elevated IGF2 levels in vivo. Increased IGF2 ligand concentration, in turn, leads to excessive activation of the biochemical cascades tied to IGF1R signaling, which, as noted above, are implicated in various cancers. Consistent with this framework, IGF2BP3 expression has been shown to be elevated in numerous cancers. See, e.g., Table 3 in Bell et al. and below.

Additionally, diagnosis of early stage cancers is a challenge for clinicians who attempt, preferably by the least invasive means, to identify malignancy confidently and with high sensitivity. For example, thyroid cancer is the most common endocrine malignancy with an estimated occurrence of >64,000 cases in the U.S. in 2016. Typically, thyroid cancer occurs in thyroid nodules which are estimated to affect >10 million people in the U.S. However, most thyroid nodules are benign, and the rate of cancer in medically evaluated thyroid nodules is only 5-10%. A clinical challenge is to accurately diagnose cancer in these nodules and to avoid unnecessary thyroid surgery for benign disease. Currently, the most reliable diagnostic tool for evaluation of thyroid nodules is fine needle aspiration (FNA) cytology. FNA provides a definitive diagnosis of benign or malignant disease in most cases. However, in approximately 25% of nodules, FNA cytology cannot reliably exclude cancer, and such cases are placed in one of the indeterminate categories: (i) atypia of undetermined significance/follicular lesion of undetermined significance (AUS/FLUS) (Bethesda III); (ii) follicular or Hurthle cell neoplasm/suspicious for follicular or Hurthle cell neoplasm (FN/SFN) (Bethesda IV); and (iii) suspicious for malignant cells (SMC) (Bethesda V). Baloch Z W et al. *Diagn Cytopathol* 2008; 36:425; Cibas E S & Ali S Z. *Am J Clin Pathol* 2009; 132:658.

Because FNA is unable to provide a definitive diagnosis for these nodules, most patients with indeterminate cytology undergo diagnostic surgery (typically a lobectomy, i.e., removal of one of the two lobes of the thyroid) to establish a histopathologic diagnosis. However, only one-third of such surgically resected thyroid nodules will prove to be malignant (PMC3698689). Overall, only 20% of thyroidectomies performed in the U.S. result in cancer diagnosis. Sosa, J A et al. *Surgery*, 2013; 154:L1420-7. These unneeded operations, with their attendant expenses and risks, may be avoided if the FNA procedure could reliably establish the pre-surgical diagnosis of a benign nodule. Moreover, those patients with indeterminate cytology for whom diagnostic lobectomy confirms a cancer frequently have to return and undergo a second surgery to "complete" the thyroidectomy. For those patients, an improved surgical management would include a single "up-front" total thyroidectomy when the diagnosis of cancer is established preoperatively. Such suboptimal clinical management, including avoidable thyroid surgeries and two-step surgeries, with the added morbidity and expenses, affect a large population of patients, as the number of thyroid FNAs with indeterminate cytologic diagnosis exceeds 125,000 each year. Sosa et al.

Molecular diagnostics for indeterminate thyroid nodules is a proven technology in the U.S., is included in major clinical practice guidelines, and is accepted by local and national insurance payers. However, currently available panels of molecular markers provided only 90% sensitivity, because not all genetic alterations in thyroid cancer are known. Although previously published panels of mutational markers included THADA (thyroid adenoma associated gene)-IGF2BP3 fusions (Nikiforov Y E, et al. "Impact of the Multi-Gene ThyroSeq Next-Generation Sequencing Assay on cancer diagnosis in thyroid nodules with atypia of undetermined significance/follicular lesion of undetermined cytology" *Thyroid* 2015; 25(11):1217-23; Nikiforov Y E, et al. "Highly accurate diagnosis of cancer in thyroid nodules with follicular neoplasm/suspicious for a follicular neoplasm cytology by ThyroSeq v2 next-generation sequencing assay" *Cancer* 2014; 120(23):3627-34), the currently available panels still suffer from a substantial portion of undetected markers. Accordingly, adding newly discovered genetic alterations to the panels will increase the sensitivity further, thus improving diagnosis and resulting patient treatment. As used herein, italics typeface denotes a gene, while plain typeface denotes a protein product of that gene.

The present inventors have identified novel genetic, mRNA, and protein biomarkers useful for prediction of therapeutic response to specific drugs and as robust and sensitive diagnostic tools for cancer detection. The present invention addresses the deficiencies of the prior art by providing methods and kits for cancer diagnosis, as well as kits and methods for the identification of cancers that are susceptible to treatment with particular pharmacological tools.

SUMMARY OF THE INVENTION

The present invention addresses the limitations currently existing within the art and provides a highly reliable and sensitive set of methods and tools for the diagnosis and treatment of cancer. The present invention takes advantage of a newly identified genetic fusion event between THADA and a region of chromosome 7 that may occur at numerous locations from zero to 65,000 bases upstream of the IGF2BP3 gene. Examples of the genetic fusion event include THADA-LOC389473, THADA-TRA2A, and THADA-position 23,511,508 on chromosome 7, among others discussed below. The genetic fusion event may result in dysregulated IGF1R signaling, as described in further detail below.

The occurrence of a genetic fusion event upstream of the IGF2BP3 gene may be evaluated using several biomarkers, including chromosomal DNA and fusion mRNA that may be isolated from a tissue sample obtained from a tumor or suspected tumor in a patient. The tissue sample may be obtained by any method commonly utilized in the art, including fine needle aspiration or biopsy. The tissue sample may be examined for those biomarkers using methods such as RT-PCR, PCR, fluorescence in-situ hybridization (FISH), or combinations of those techniques to evaluate the occurrence of the genetic fusion events.

On the basis of the evaluation of those biomarkers, the present invention provides methods for the reliable and sensitive diagnosis of cancer or cancerous tumors. If the genetic fusion events are observed in the DNA and/or RNA isolated from tissue sample, then one may conclude with confidence that the tumor or suspected tumor is cancerous.

The diagnostic methods of the present invention may also include extracting protein from the tissue sample and testing for the expression of an IGF2BP3 fusion protein (i.e., protein expressed as a result of the genetic fusion event) using such techniques as in situ immunohistochemistry, Western blot analysis, or other methods capable of measuring the amount of protein present. By conducting this analysis, one of skill in the art may establish elevated levels of the IGF2BP3 fusion protein compared to normal tissue, thus additionally permitting the diagnosis of the tumor or suspect tumor as cancerous.

The present invention further provides methods of selecting a patient with a tumor or suspected tumor for therapeutic intervention for the treatment of that tumor. Specifically, these embodiments of the present invention may again employ a tissue sample obtained from a tumor or suspected tumor in a patient by such techniques as fine needle aspiration or biopsy. The tissue sample may be evaluated for a biomarker that is reflective of the occurrence of a genetic fusion event upstream of the IGF2BP3 gene or the occurrence of IGF2BP3 protein overexpression, when compared to normal tissue. If evidence of the genetic fusion event is found, either in genomic DNA or mRNA using such techniques as RT-PCR, PCR, or FISH, or if IGF2BP3 protein is elevated compared to normal tissue, then the patient is identified as a potential candidate for the treatment of cancer using therapeutic agents that disrupt IGF1R signaling.

In some embodiments of the present invention, the patient may be subsequently treated for cancer by providing those therapeutic agents that disrupt IGF1R signaling. A therapeutic intervention utilizing such therapeutic agents may employ such agents as monoclonal antibodies, small molecule inhibitors, and combinations thereof. Examples of suitable monoclonal antibodies include those which are targeted to either IGF1R, such as figitumumab, cixutumumab, AMG-479, BIIB022, dalotuzumab, robatumumab, and F 50035, and monoclonal antibodies directed to IGF1/2 peptide ligands, such as Medi-573. Suitable small molecule inhibitors of IGF1R signaling include BMS-754807, linsitinib, XL228, AXL1717, INSM-18, and NVP AEW541.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 2A shows levels of THADA mRNA expression in normal tissue, fusion-negative tumors, and fusion-positive tumors;

FIG. 2B shows levels of IGF2BP3 mRNA expression in normal thyroid tissue, fusion-negative tumors, and fusion-positive tumors;

FIG. 3A displays a Western blot analysis demonstrating overexpression of IGF2BP3 and IGF2 in transfected FTC133 cells and also shows the increase in proliferation of transfected FTC133 cells;

FIG. 3B displays a Western blot analysis demonstrating overexpression of IGF2BP3 and IGF2 in transfected HEK293 cells and also shows the increase in proliferation of transfected HEK293 cells;

FIG. 3C displays a Western blot analysis demonstrating overexpression of IGF2BP3 in transfected U2OS cells and also shows the increase in proliferation of transfected U2OS cells;

FIG. 3D displays the impact of silencing IGF2BP3 translation with siRNA on cell proliferation in PaCa-2 cells;

FIG. 5A shows the impact of IGF1R inhibition on the phosphorylation state of several proteins;

FIG. 5B demonstrates the impact of IGF1R inhibition on cell growth in several cell types;

FIG. 5C demonstrates the impact of IGF1R inhibition on cell growth in IGF2BP3 transfected cells;

FIG. 5D demonstrates the impact of IGF1R inhibition on cell migration and invasion of PaCa-2 cells;

FIG. 5E displays data demonstrating rescue of the effects of IGF1R inhibition by supplementing the culture medium with IGF2 ligand;

FIG. 5F shows the results of xenograft experiments using cancer cell types with overexpression of IGF2BP3 treated with IGF1R inhibitor; and FIG. 5G shows the results of xenograft experiments using cell types with no expression of IGF2BP3 treated with IGF1R inhibitor.

DETAILED DESCRIPTION OF THE INVENTION

The present invention addresses the limitations currently existing within the art and provides novel methods and tools for the diagnosis of cancer that rely, in part, upon the surprising discovery that previously unknown genetic fusion events result in elevated expression of IGF2BP3 in a subpopulation of cancers. These observations provide for novel methods of identifying populations of cancer patients whose tumors express high levels of IGF2BP3 for subsequent therapeutic intervention using disruptors of IGF1R signaling.

The present inventors have identified recurrent fusions between the THADA gene on chromosome 2 to several regions on chromosome 7 that result in increased expression of a downstream IGF2BP3 gene. In turn, increased expression of the IGF2BP3 protein, results in elevated expression of the signaling molecule IGF2 and other proteins by binding to target mRNAs and controlling their stability and translation. The resulting increased levels of the ligand IGF2, in turn, markedly increase IGF2-dependent signaling through IGF1R receptors, resulting in malignant neoplastic growth. Thus, the novel genetic fusion events identified by the present inventors transform normal cellular biochemical activity into dysregulated IGF1R-dependent cancerous cellular growth.

The present invention takes advantage of this discovery by providing for tools useful in diagnosing relatively early stage cancers. These diagnostic tools may employ either genetic, fluorescence in-situ hybridization (FISH), or immunohistochemical techniques to identify cancers with high sensitivity and high confidence at early stages. Specifically, improved diagnostic panels are provided that may assess the occurrence of the identified genetic fusion events and/or the expression levels of IGF2BP3 protein in isolated tumor cells to permit confident diagnosis. Furthermore, these techniques may be employed in conjunction with currently available diagnostic panels to dramatically improve diagnostic sensitivity, thus improving subsequent patient treatment.

While the invention is described with particular reference to particular cancers and with respect to specific genetic fusion events, it is noted that the methods and tools disclosed herein have general applicability and are not limited to those examples utilized for purposes of the present description.

Figure 1A:
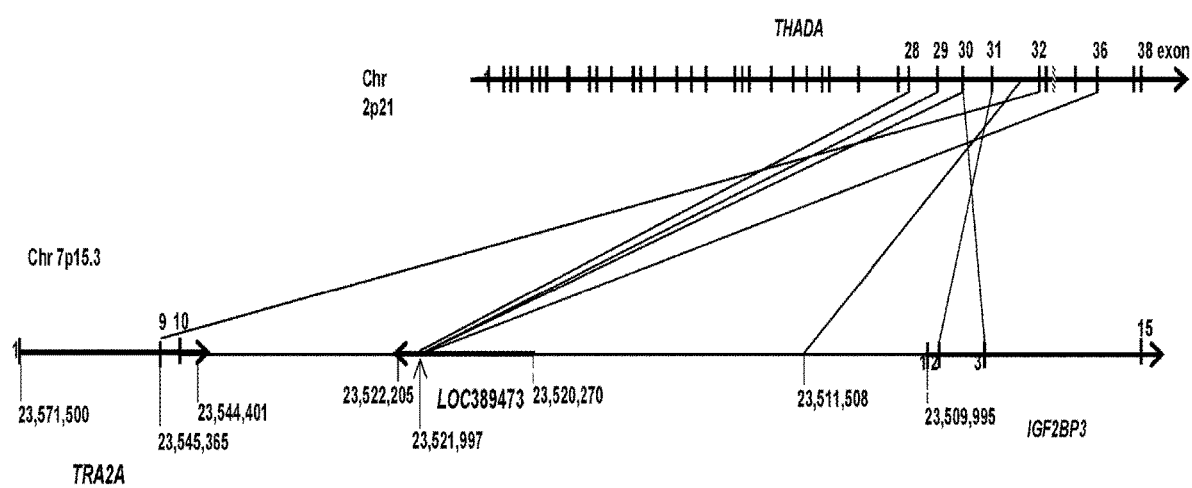
FIG. 1A is a schematic representation of location of the fusion points between the THADA gene and multiple locations upstream of the IGF2BP3 gene, where chromosomal locations are shown based on based on genome build 37 UCSC/genome browser version 19.

In an effort to identify novel biomarkers for particular types of thyroid cancer, the present inventors employed tissue from papillary thyroid carcinoma (PTC). A pre-screened group of 25 PTCs lacking all known mutations was studied by whole transcriptome (RNA-seq; 21 tumors) or whole genome sequencing (WGS; 4 tumors) using paired-end sequencing on ILLUMINA HiSeq. Using RNA-Seq, six tumors were found to have gene fusions involving the THADA gene located on 2p21. In four tumors, RNA-Seq results revealed fusions between different exons (28, 29, 30 or 36) of THADA and a breakpoint located 12 kb upstream of the IGF2BP3 gene and in the putative *Homo sapiens* gene LOC389473 on 7p15.3 (chr. position 23,521,997) (FIG. 1A and Table 1). FIG. 1A displays a scheme of gene fusions identified in those six thyroid cancers at both the mRNA and DNA levels.

TABLE 1

Thyroid tumor samples with THADA fusions identified by RNA-Seq or WGS analysis.

| Tumor sample | Detection Mode | Fusion partners 5' | 3' |
| --- | --- | --- | --- |
| T1 | RNAseq | THADA exon 30 | LOC389473 |
| T2 | RNAseq | THADA exon 36 | LOC389473 |
| T3 | RNAseq | THADA exon 29 | LOC389473 |
| T4 | RNAseq | THADA exon 30 | IGF2BP3 exon 3* |
| T5 | RNAseq | THADA exon 28 | LOC389473 |
| T6 | RNAseq | THADA exon 31 | IGF2BP3 exon 2 |
| T7 | WGS | THADA intron 31 | 1.5 kb upstream of IGF2BP3 |

Figure 1B:
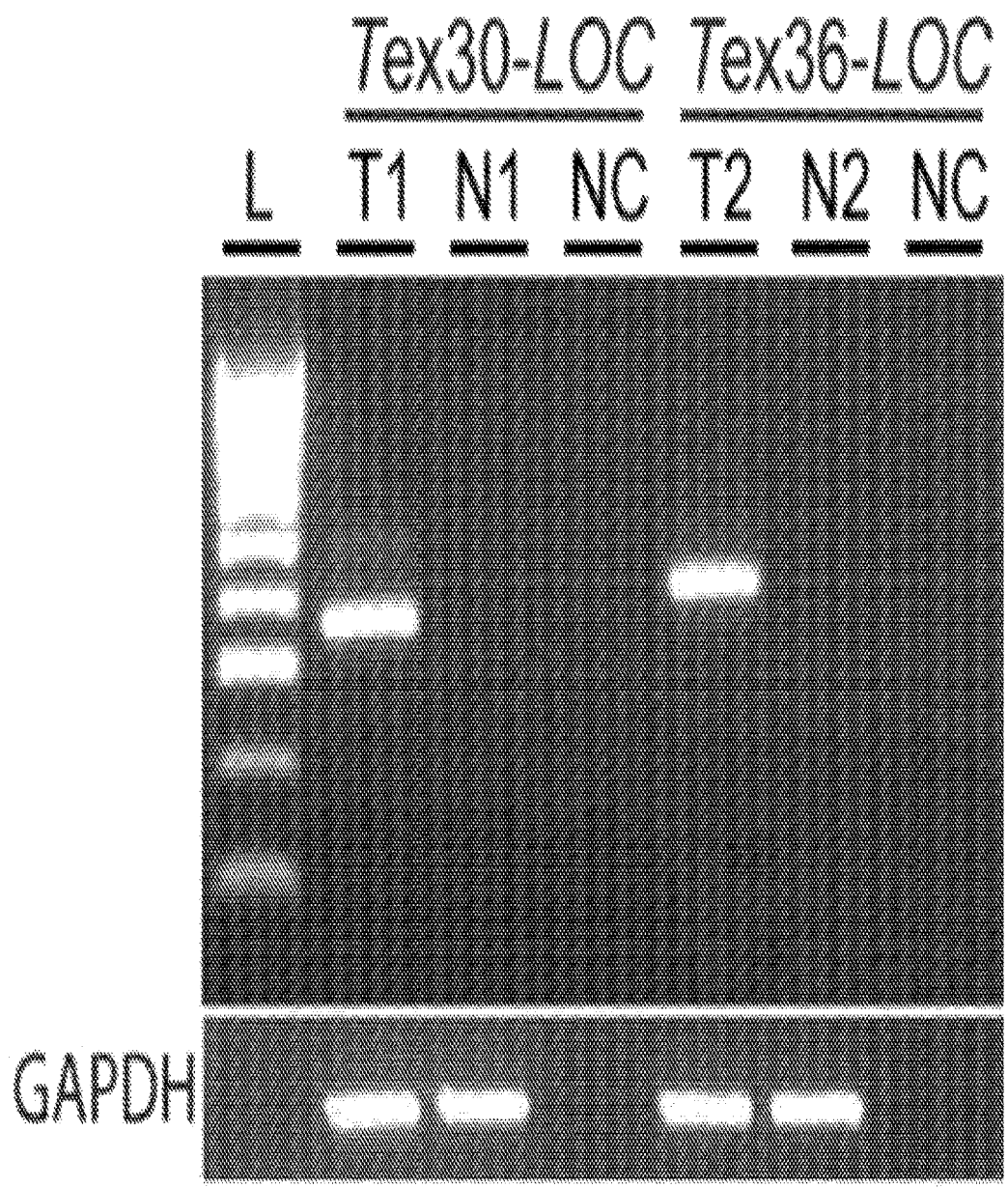
FIG. 1B shows a gel demonstrating the presence of fusions as detected by RT-PCR (reverse transcriptase-polymer chain reaction)
Figure 1C:
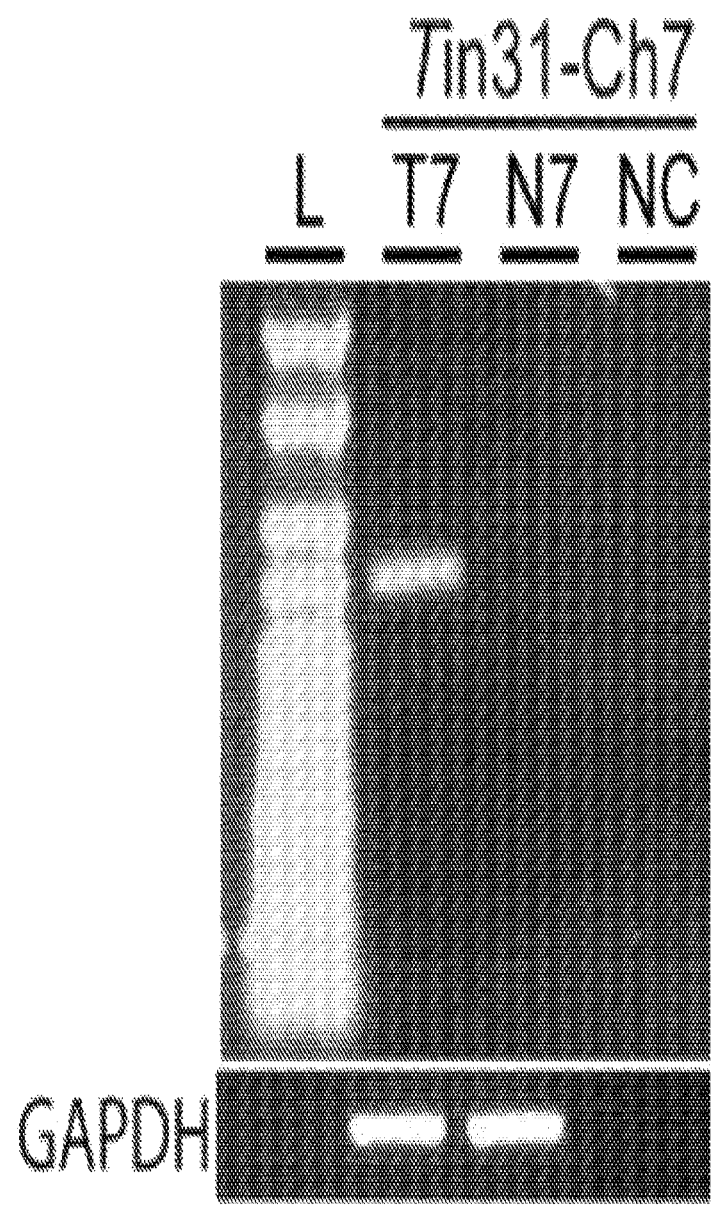
FIG. 1C displays a gel demonstrating the presence of fusions as detected by PCR.

RNA-Seq analysis of the other two tumors revealed fusions between exon 30 of THADA and exon 3 of IGF2BP3 or between exon 31 of THADA and exon 2 of IGF2BP3. All fusions were confirmed by RT-PCR and Sanger sequencing, as shown in the gels of FIG. 1B. Using WGS, one additional tumor was found to have a fusion between intron 31 of THADA and a region located 1.5 kb upstream of the IGF2BP3 gene (chr. position 23,511,508 based on genome build 37 UCSC/genome browser version 19 (FIG. 1A). The fusion was confirmed by PCR and Sanger sequencing of tumor DNA, as shown in the gels of FIG. 1C. The t(2;7) rearrangement was further confirmed by fluorescence in situ hybridization (FISH) in each of the five tumors studied. A listing of primers useful for the detection of particular fusion events via RT-PCR may be found in Table 2.

Further, it was found that THADA also formed additional genetic fusions with TRA2A and other non-coding DNA regions in numerous locations from zero to 65 kilobases upstream of the IGF2BP3 gene (FIG. 1A). In each of these instances, observation of the genetic fusion events correlated with overexpression of IGF2BP3 protein, consistent with the remainder of observations presented here.

The investigation of the impact of those genetic fusions on protein expression was subsequently performed. The THADA-LOC389473 fusion places the partner genes in the head to tail orientation and they transcribe in opposite directions, so the fusion mRNA contain a stop codon downstream of the fusion point in all four tumors, suggesting that THADA-LOC389473 is unlikely to yield a functional protein. This, together with finding the THADA-IGF2BP3 fusions in other tumors led to the hypothesis that THADA-LOC389473 may affect carcinogenesis instead via altering the IGF2BP3 gene or its expression. To test this, the expression levels of THADA and IGF2BP3 in normal thyroid tissues and tumors by RT-qPCR were detected. The analysis showed that THADA was expressed at high level in normal thyroid follicular cells as compared to other cell types studied, and its expression was not altered in thyroid cancers positive or negative for THADA fusions (FIG. 2A). The expression levels (mean±SD) of THADA mRNA detected by RT-qPCR indifferent indicated tissues (n=4 for each tissue type), thyroid C cell-derived tumor cell line TT1, and thyroid tumors negative (n=6) and positive (n=6) for THADA fusions (tumors T1, T2, T4-T6, T7) are presented in FIG. 2A.

In contrast, IGF2BP3 mRNA was found to be expressed at a very low level in normal thyroid cells and tumors negative for the fusion, but its expression was increased 90-102 fold in all tumors carrying the fusion (FIG. 2B). Similar findings were observed in the RNA-Seq data, which showed the increased expression of the full-length IGF2BP3 mRNA in tumors positive for THADA-LOC389473 and

TABLE 2

Listing of primers.

| Primer | Sequence (5'-3') | SEQ ID No. |
| --- | --- | --- |
| THADA-upstream of IGF2BP3 fusions | | |
| THADA exon 28 F* | ATGGGAGAACCAAATCGTCA | SEQ ID No. 1 |
| THADA exon 29 F | TGTCTACCACTCCCGTGAAA | SEQ ID No. 2 |
| THADA exon 30 F | CTCAGACTCCAAACACGGAAC | SEQ ID No. 3 |
| THADA exon 36 F | TTGCAGGATACACTTGCTCTCT | SEQ ID No. 4 |
| up-stream IGF2BP3 R | GCTCCCAACGAAATGGATAA | SEQ ID No. 5 |
| THADA-upstream IGF2BP3 DNA F | CCAAAGGAATGAGGCTGAAT | SEQ ID No. 6 |
| THADA-upstream IGF2BP3 DNA R | TTTTCTACCAGTAAGAGTACCAAGTCA | SEQ ID No. 7 |
| up-stream IGF2BP3/ THADA DNA F | ATACGGAAACGAAGGCAGTG | SEQ ID No. 8 |
| up-stream IGF2BP3/ THADA DNA R | TGCTTGTGCATTTGATTTCAT | SEQ ID No. 9 |
| TRA2A R | AAGGGAATCCCGTTATCAGC | SEQ ID No. 10 |
| THADA-IGF2BP3 fusions | | |
| THADA exon 30 F | CTCAGACTCCAAACACGGAAC | SEQ ID No. 11 |
| THADA exon 31 F | GCAAAATCCATGTTTGGTGA | SEQ ID No. 12 |
| THADA exon 32 F | CGATCACCTTCTCCTTATTATAGTCG | SEQ ID No. 13 |
| THADA exon 36 F | TTGCAGGATACACTTGCTCTCT | SEQ ID No. 14 |
| IGF2BP3 exon 1 R | AACGCGTAGCCAGTCTTCAC | SEQ ID No. 15 |
| IGF2BP3 exon 2 R | GGACCGAGTGCTCAACTTCT | SEQ ID No. 16 |
| IGF2BP3 exon 4 R | ACAGCTCTCCACCACTCCAT | SEQ ID No. 17 |

Figure 2C:
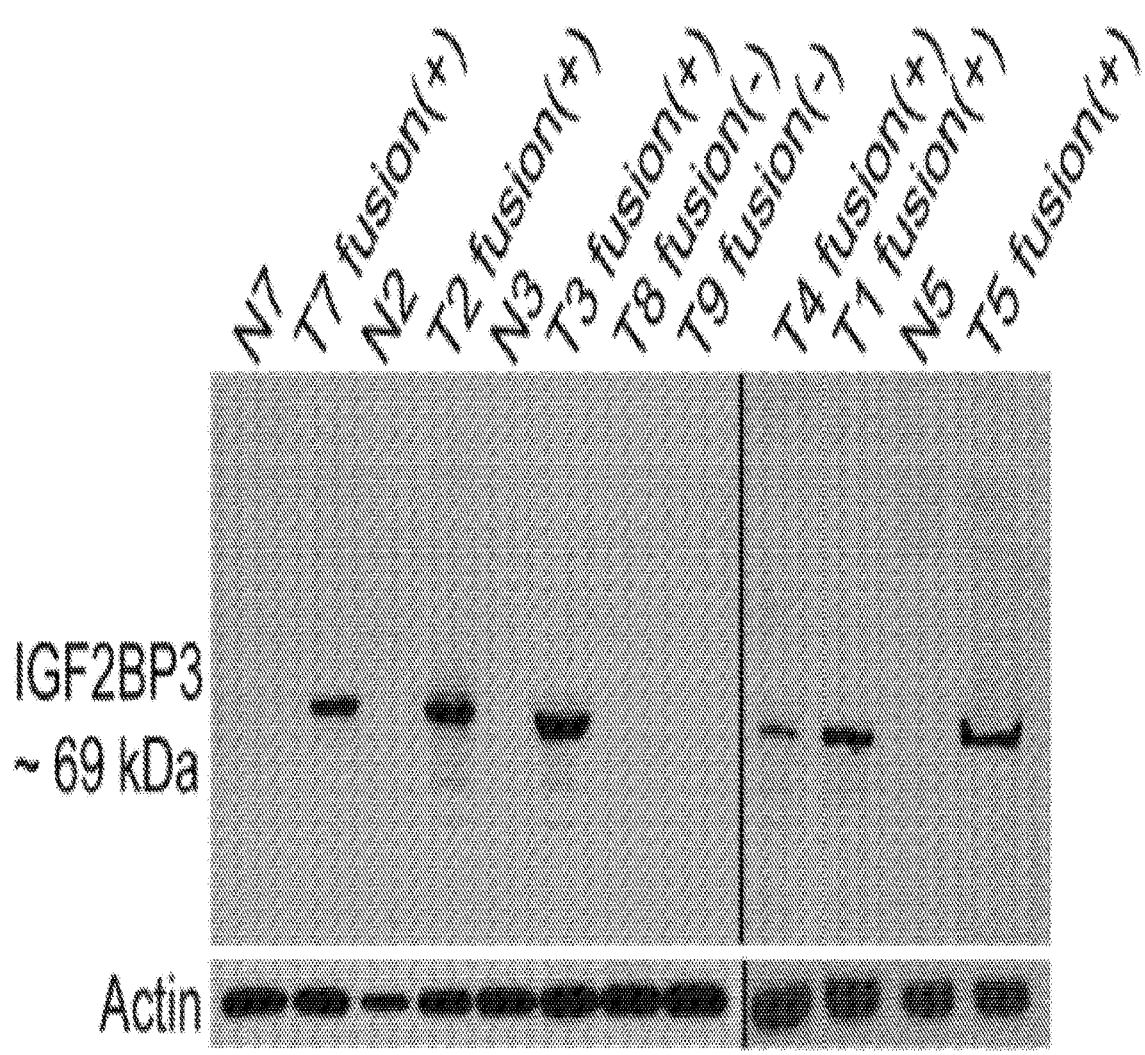
FIG. 2C displays a Western blot demonstrating detection and overexpression of IGF2BP3 protein in tumor cells.
Figure 2D:
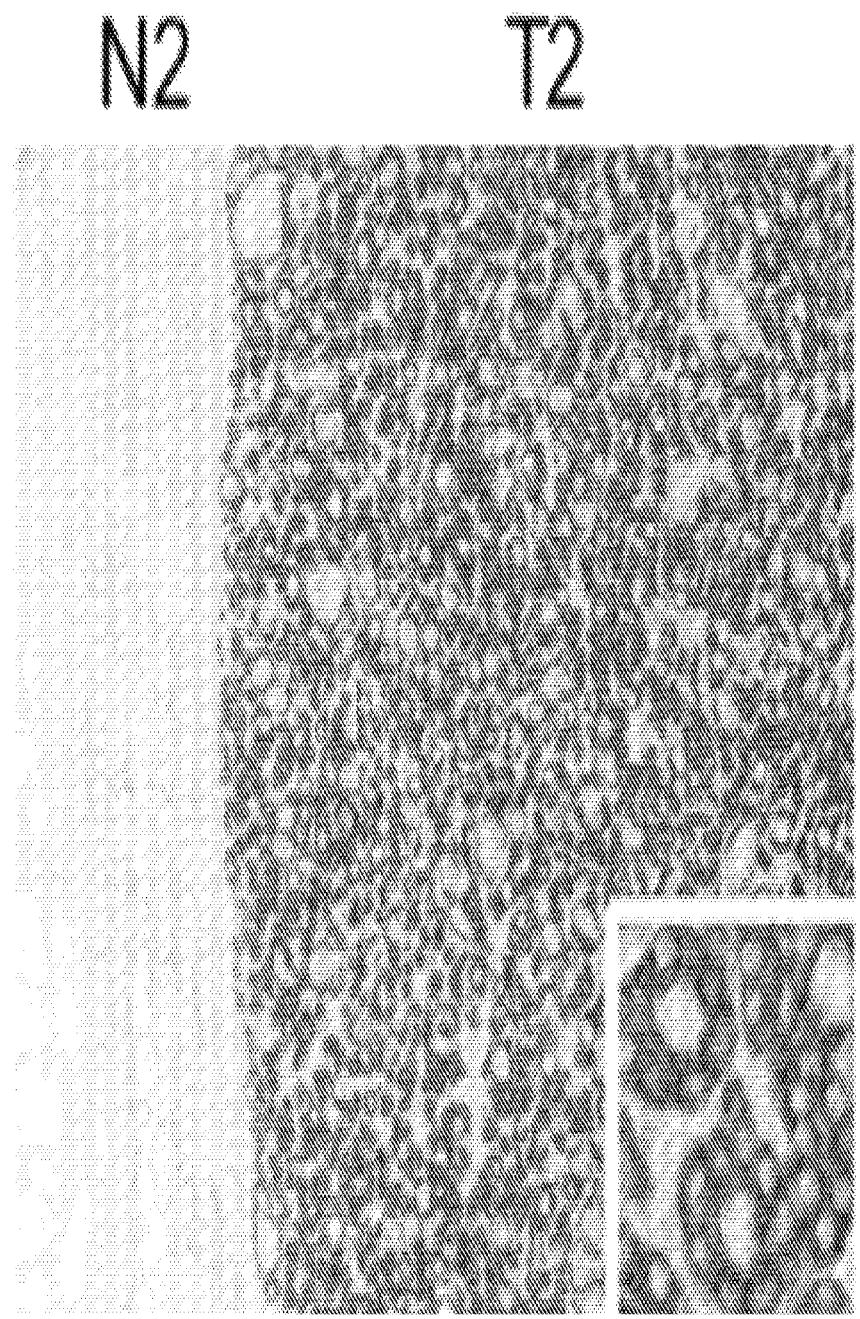
FIG. 2D displays the results of immunohistochemical analysis demonstrating detection of IGF2BP3 protein overexpression in tumor cells.

*-"F" designates a forward-reading primer, while "R" designates a reverse reading primer THADA-IGF2BP3 fusions. Similarly, by Western blotting analysis, all six tumors studied showed high levels of IGF2BP3 protein of ~69 kDa molecular weight, corresponding to full length IGF2BP3 protein, and no other protein products that would correspond to a chimeric gene product, as shown in FIG. 2C. The analysis included tumors with THADA-LOC389473, THADA-IGF2BP3, and THADA-1.5 kb upstream of IGF2BP3 fusions. Further, the immunohistochemical analysis with IGF2BP3 antibody showed strong cytoplasmic immunoreactivity in all studied fusion-positive tumors, but not in adjacent normal thyroid tissue, as exemplified in FIG. 2D, which shows strong cytoplasmic immunoreactivity with anti-IGF2BP3 antibody in the tumor (T2) and complete lack of staining in adjacent normal thyroid tissue (N2). These data indicate that fusion between the THADA gene and LOC389473, a predicted gene located 12 kb upstream of the IGF2BP3 gene, is unlikely to produce a functional chimeric gene, but instead results in strong overexpression of the full-length IGF2BP3 transcript and protein, likely due to juxtaposition of the IGF2BP3 chromosomal locus on 7p15.3 to the actively transcribed THADA locus on 2p21.

After establishing that the observed genetic fusions resulted in elevated levels of IGF2BP3 protein, evaluation of that elevated protein expression on downstream protein expression events was evaluated. As discussed above, IGF2BP3 is known to serve as a translational activator of IGF2 mRNA. Therefore, the expression of IGF2 mRNA and protein was evaluated in thyroid tumors positive and negative for THADA fusions. Using quantitative RT-PCR, no difference in IGF2 mRNA levels was detected. Using Western blotting, a significant increase in IGF2 protein was found in all tested tumors positive for the fusion and IGF2BP3 overexpression.

IGF2 is known to act as an autocrine and paracrine regulator of IGF1R, leading to activation of the PI3K and MAPK signaling pathways. Therefore, tests were undertaken to determine whether the increase in IGF2 protein in these human tumor tissues was associated with the increased phosphorylation of AKT and ERK proteins. Using Western blot analysis, increased pAKT and pERK in all tumors positive for the fusion was observed. The effect of IGF2BP3 overexpression on IGF2 signaling was further confirmed in vitro. Overexpression of IGF2BP3 in HEK293 cells led to the increase in IGF2 protein and increased phosphorylation of AKT and ERK proteins. Knockdown experiments were performed in PaCa-2 pancreatic cancer cells that have a very high level of IGF2BP3 expression based on the reference database for gene expression analysis (LSBM), which was confirmed by Western blot and immunohistochemistry. Knockdown of IGF2BP3 using siRNA led to a significant reduction in IGF2 protein levels and decreased phosphorylated AKT and ERK, confirming the impact of IGF2BP3 on translational activation of IGF2 and its downstream signaling.

To study the biological effect of THADA fusions and IGF2BP3 overexpression in thyroid and other cell types, full-length IGF2BP3 mRNA was overexpressed in FTC133, HEK293, and U2OS cells, which all endogenously express low levels of IGF2BP3. Overexpression of IGF2BP3 resulted in a significant increase in proliferation in all three cell lines (FIGS. 3A-C). Specifically, FIGS. 3A-C shows overexpression of IGF2BP3 confirmed by Western blot analyses 24 hours post-transfection in FTC133 (FIG. 3A), HEK293 (FIG. 3B), and U2OS (FIG. 3C) cells resulted in increased cell proliferation in each cell type. Data from experiments repeated in quadruplicate are shown as mean±SD ($P<0.01$, *$P<0.001$, ****$P<0.0001$; 2-tailed Student's t test in FIG. 3, all subparts). In a reverse experiment, silencing of IGF2BP3 using siRNA knockdown of IGF2BP3 expression in PaCa-2 cancer cells that have high levels of IGF2BP3 expression led to a significantly reduced growth rate (FIG. 3D).

Next, the impact of IGF2BP3 overexpression on cell migration and invasion was investigated. Using a wound healing assay, IGF2BP3 overexpression in HEK293 cells led to significantly faster cellular migration, whereas IGF2BP3 knockdown in PaCa-2 cells resulted in decreased cell migration. Similarly, a Matrigel invasion assay showed that overexpression of IGF2BP3 in HEK293 led to a significant enhancement of cell invasion, and the knockdown of IGF2BP3 in PaCa-2 cells resulted in reduced cell invasiveness.

Finally, the impact of IGF2BP3 overexpression on cell transformation was investigated. Using a soft agar colony formation assay, FTC133 thyroid cells transfected with an IGF2BP3 vector showed significant increases in colony formation in the soft agar as compared to empty vector, indicating enhanced anchorage-independent growth, a characteristic of transformed cells. In a reverse experiment, knockdown of IGF2BP3 expression in PaCa-2 cancer cells resulted in significant reduction of colony formation in the soft agar. Together, these data indicate that IGF2BP3 overexpression promotes cell proliferation, migration, invasion, and transformation in thyroid and other cell types.

To evaluate the rate of IGF2BP3 alterations in thyroid tumors, an immunohistochemistry (IHC) assay for specific and sensitive detection of overexpression of IGF2PB3 protein in tumors carrying THADA-LOC389473 and THADA-IGF2BP3 fusions was developed. For this, IHC for IGF2PB3 was titrated using 7 fusion-positive and 18 fusion-negative thyroid cancers to achieve strong and diffuse cytoplasmic immunoreactivity in all positive cancers and complete absence of immunoreactivity in fusion-negative cancers. Further, targeted next generation sequencing (NGS) was used for quantitative assessment of IGF2BP3 mRNA. Analysis of 192 PTC, which represented a series of consecutive tumors with this diagnosis analyzed by targeted NGS, revealed 10 (5.2%) cases with strong IGF2BP3 immunoreactivity, all were confirmed to have high level of IGF2PB3 mRNA expression. Using RT-PCR, 9 out of 10 (90%) tumors were positive for a fusion, typically THADA-LOC389473. Rearrangement involving the IGF2BP3 region was further confirmed by FISH in all 10 IHC-positive thyroid cancers. This result demonstrated high specificity of the IHC assay in detecting tumors with IGF2BP3 overexpression caused by chromosomal rearrangements. It also showed that chromosomal rearrangement involving THADA fused to a chromosomal region upstream of IGF2BP3 is a dominant mechanism of IGF2BP3 overexpression in PTC.

Next, the clinical and phenotypic features of thyroid cancers that showed IGF2BP3 overexpression were evaluated. These tumors were characterized by slight female predominance (1.5:1), mean patient age of 48.9 years, and tumor size ranging from 1.6 to 9 cm (mean, 3.8 cm). Despite large tumor size, microscopically, the tumors were either encapsulated (n=5) or well circumscribed (n=5) with the follicular growth pattern characteristic of the follicular variant of PTC or non-invasive follicular thyroid tumor with papillary-like nuclear features (NIFTP). None of them showed other common driver mutations known to occur in thyroid cancer (e.g., BRAE, RAS), providing additional evidence for THADA-LOC389473 and THADA-IGF2BP3 fusions being a newly identified driver event in tumors.

Figure 4:
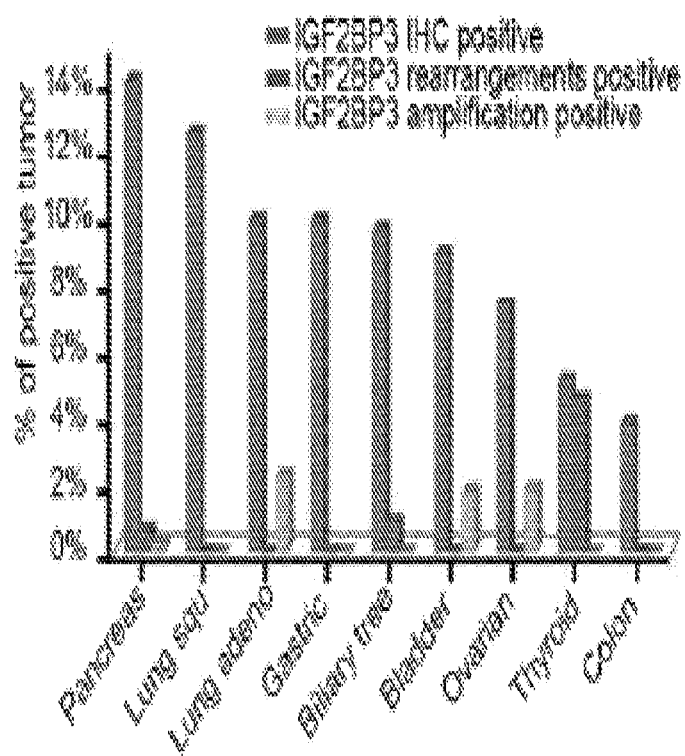
FIG. 4 displays the frequency of IGF2BP3 overexpression in several common cancer types detected by immunohistochemistry.

Further, the frequency of IGF2BP3 overexpression and its mechanisms in other cancer types was evaluated. Using the IGF2BP3 IHC assay described above to screen tissue microarrays of 12 common cancer types, strong and diffuse immunoreactivity was found in 14.2% pancreatic cancers, 12.6% lung squamous cell carcinomas, 10.1% lung adenocarcinomas, 10% gastric cancers, 9.7% cholangiocarcinomas, 9.1% bladder cancers, 7.5% ovarian cancer, and 3.8% colon cancers (FIG. 4 and Table 3).

TABLE 3

Frequency of IGF2BP3 immunoreactivity and IGF2BP3 gene locus rearrangement and amplification detected by FISH in different cancer types.

| Cancer types (n = cases) | IGF2BP3 IHC | IGF2BP3 rearrangements (among IHC-positive tumors) | IGF2BP3 Amplification (among IHC-positive tumors) |
|---|---|---|---|
| Pancreas (n = 331) | 47/331 | 2/8 (25%) | 1/8 (12.5%) |
| Lung squamous cell (n = 119) | 15/119 (12.6%) | 0/5 | 0/5 |
| Lung adenocarcinoma (n = 129) | 13/129 (10.1%) | 0/18 | 3/18 (16.7%) |
| Gastric (n = 30) | 3/30 (10%) | | |
| Biliary tree (n = 113) | 11/113 (9.7%) | 1/4 (25%) | 0/3 |
| Bladder (n = 55) | 5/55 (9.1%) | 0/5 | 1/5 (20%) |
| Ovarian (n = 53) | 4/53 (7.5%) | 0/4 | 1/4 (25%) |
| Thyroid (n = 192) | 10/192 (5.2%) | 9/10 (90%) | 0/5 |
| Colon (=78) | 3/78 (3.8%) | 0/3 | 0/3 |

Using FISH analysis of selected IHC-positive cancers, chromosomal rearrangements involving the IGF2BP3 region were identified in 3/12 (25%) pancreatobiliary cancer, and IGF2BP3 amplification in 3/18 (16.7%) IHC-positive lung adenocarcinomas, 1/8 (12.5%) pancreatic and 1/5 (20%) bladder cancers (FIG. 4 and Table 3). This suggests that in addition to gene fusions, many non-thyroid cancers have IGF2PB3 overexpression, which may be due to gene amplifications or other, possibly epigenetic, mechanisms, such as aberrant methylation. Overall, these data demonstrate that strong overexpression of IGF2PB3, driven by gene fusions as well as other genetic and possibly epigenetic mechanisms, occur in a distinct subset of not only thyroid, but also other, cancer types.

These results demonstrate that the observations obtained using thyroid cancer cells as a model system possess general utility to a subset of cancers as a diagnostic tool. Generally, these diagnostic tools may be utilized to detect cancer or precancerous regions in thyroid nodules or other types of cancer. For example, the THADA-LOC389473 fusion (involving chromosome 7 position 23,521,997) which results in overexpression of IGF2BP3 (or other genetic fusion events, e.g., THADA-TRA2A) may be added to commonly available diagnostic panels. Such genetic fusions are detected in 5% of thyroid tumors, and the addition of this assay component will improve the sensitivity obtained by currently employed panels, where 10% of cancerous tumors are misdiagnosed as false negatives, by approximately 5%, thus further reducing misdiagnoses by approximately 50%. Such genetic assessments may be conducted by next generation sequencing, Sanger sequencing, Maxam-Gilbert sequencing, hybridization, or other known genetic tools.

Similarly, overexpression of IGF2BP3 mRNA, alone or in combination with other biomarkers disclosed herein, as assessed through, for example, RT-PCR may be utilized as a diagnostic criterion for cancer diagnosis. Additionally, the measurement of IGF2BP3 protein levels as assessed using immunohistological tools may also serve as a valuable diagnostic tool, as the results here demonstrate that elevated levels of IGF2BP3 correlate with malignancy. The DNA, RNA, and/or protein samples for use in these novel methods and panels may be obtained from patients using well-known techniques. Thus, embodiments of the present invention incorporate information regarding newly discovered biomarkers into established bioassay panels to substantially improve their sensitivity, reliability, and general utility.

The effects of IGF1R inhibition on the growth of cancer cells driven by IGF2PB3 overexpression were then tested. First, studies were conducted to determine if activation of the AKT and MAPK pathways and cell growth induced by IGF2BP3 overexpression is affected by inhibiting IGF1R by OSI-906 in vitro. FIG. 5A displays the results of treatment with 5 μM of IGF1R inhibitor (OSI-906) for 30 minutes led to the inhibition of IGF1R phosphorylation and downstream signaling in HEK293 cells induced by IGF2BP3. Western blotting showed that inhibition of IGF1R blocked phosphorylation of AKT, S6, and ERK induced by IGF2BP3 overexpression in HEK293 cells (FIG. 5A). Further, it was observed that inhibition of IGF1R by OSI-906 led to dose-dependent growth inhibition of PaCa-2 cancer cells, which strongly overexpress IGF2BP3, but did not have any effects on FTC133 and U2OS cells with low levels of IGF2BP3 expression (FIG. 5B). The bottom panel of FIG. 5B shows the impact of treatment of the specified cells with OSI-906 for 72 hours, which resulted in inhibition of proliferation of PaCa-2 cells expressing IGF2BP3 at a high level, but no effect on proliferation of FTC133 and U2OS cells that lack IGR2BP3 expression. The experiments were repeated in quadruplicate and were calculated as percentage of viable cells after treatment with OSI-906 (mean±SD). However, when IGF2BP3 expression was induced in FTC133 and U2OS cells by transient transfection, both cell types acquired sensitivity to growth inhibition by OSI-906, and subsequent inhibition of IGF1R returned the cells to an IGF2BP3-negative-like state (FIG. 5C). Similar effects of IGF1R inhibition were observed on migration and invasion of PaCa-2 cells (FIG. 5D) that were treated with 1 μM OSI-906 or vehicle, as indicated. Again, the assay was performed in quadruplicate and shown as mean±SD. Further, OSI-906 treatment of PaCa-2 cells led to significant reduction of colony formation in soft agar.

To determine if the inhibitory effect of OSI-906 on cell proliferation is mediated by the ligand IGF2, whether the inhibition of PaCa-2 cell proliferation following IGF2BP3 knockdown can be rescued by IGF2 was evaluated. Indeed, the reduction in PaCa-2 cell growth by IGF2BP3 siRNA was reversed after supplementing the cell culture medium with sufficient concentration of exogenous IGF2 (FIG. 5E). The assay was performed in quadruplicate and shown in FIG. 5E as mean±SD (*$P<0.05$; 2-tailed Student's t test).

Next, tumor cells overexpressing IGF2BP3 were tested to see if their growth can be blocked via IGF1R inhibition in vivo using a xenograft experimental model. Pancreatic cancer cells PaCa-2 and colon cancer cells Caco-2, both expressing IGF2PB3 at high level (FIG. 5B), and thyroid cancer cells FTC133 with low levels of IGF2BP3 expression were employed to establish tumors growing in nude mice at sites of subcutaneous cell injection. Treatment of mice with therapeutic doses of OSI-906 arrested growth of tumors originated from PaCa-2 and Caco-2 cells (FIG. 5F), but had no effect on the growth of the FTC133-derived tumors (FIG. 5G). The inhibitory effect on tumor growth coincided with the reduction of phosphorylated IGF1R, AKT, S6, and ERK in the tumor tissue (FIG. 5F), whereas tumors originated from FTC133 and lacking IGF2BP3 expression did not show reduction in the phosphorylation of these proteins (FIG. 5G). These data show that growth of cancer cells overexpressing IGF2BP3 can be arrested by IGF1R inhibitors in vitro and in vivo, providing evidence for a benefit of anti-IGF1R therapy in cancers with strong overexpression of IGF2BP3.

As noted above, in clinical trials of OSI-906 (linsitinib; an IGF1R signaling inhibitor), clinical response was registered in only a small proportion (1-5%) of patients with solid tumors. As described above, the present invention demonstrates that growth of xenografts in nude mice of human colon and pancreatic cancer cells that are dependent on IGF2BP3 upregulation are particularly inhibited by administration of a therapeutic dosage of linsitinib. In contrast, the growth xenografts of non-IGF2BP3 dependent human thyroid cancer cells are not impacted by linsitinib administration.

Thus, the present invention encompasses tools and methods that permit the identification of cancers that are susceptible to therapeutic intervention by agents that disrupt IGF1R signaling. The preselection of such cancers is expected to dramatically improve the outcome by tailoring therapeutic intervention to those agents that are likely to be effective in those types of cancer. This preselection or identification of cancers may be achieved by the assessment of the occurrence of genetic fusion events up to 65,000 bases upstream of the IGF2BP3 gene. This evaluation may be accomplished by evaluating genomic DNA, fusion mRNA, or IGF2BP3 mRNA or protein.

The present invention also provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and squamous cell carcinoma and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia, multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoacanthoma, seminoma, thyroid follicular cancer, teratocarcinoma, chemotherapy refractory non-seminomatous germ-cell tumors, and Kaposi's sarcoma, and any metastasis thereof.

In particular, the present methods and tools are particularly well suited for application in those cancers where genetic fusion events (e.g., THADA-LOC389473) are observed and, moreover, to cancers where elevated IGF2BP3 protein levels are observed. In particularly useful embodiments, the methods and tools of the present invention are well suited to the diagnosis and treatment of thyroid cancer, pancreatic cancer, colon cancer, lung cancer, gastric cancer, bladder cancer, ovarian cancer, biliary tree cancer, and other cancers where elevated IGF2BP3 or genetic fusion events are observed. Certain particularly preferred embodiments of the present invention are particularly useful in the diagnosis and treatment of thyroid cancer, pancreatobiliary cancer, gastric cancer, ovarian cancer, colon cancer, and lung cancer. See Table 3 above.

The present invention further provides for selective identification of patients whose cancers may be particularly responsive to inhibition of IGF1R signaling. As described above, studies of xenograft tumors demonstrated a robust correlation between overexpression of IGF2BP3 and responsiveness to disruption of IGF1R signaling (e.g., by linsitinib). This observation provides an explanation for the consistently variable responsiveness observed in clinical trials where IGF1R signaling is disrupted by small molecule or antibody inhibitors. S. J. Weroha & P. Haluska "IGF-1 Receptor Inhibitors in Clinical Trials—Early Lessons" *J Mammary Gland Biol Neoplasia* 2008 December; 13(4): 471-83; U.S. Patent Application Publication No. 2012/0220594; Jones, R. L., et al. "Phase I study of intermittent oral dosing of the insulin-like growth factor-1 and insulin receptors inhibitor OSI-906 in patients with advanced solid tumors." *Clin Cancer Res* 21: 693-700 (2015); and Yee, D. "Insulin-like growth factor receptor inhibitors: baby or the bathwater?" *J Nat Cancer Inst* 104: 975-981 (2012), which are hereby incorporated by reference for the lists of chemotherapeutic agents that disrupt IGF1R signaling.

In particular, the present invention provides for the pre-screening of cancer patients, whereby the levels of IGF2BP3 fusion protein, the presence of fusion mRNA, and/or presence of genomic fusion events up to 65,000 bases upstream of the IGF2BP3 gene may be assessed prior to treatment initiation. Specifically, a sample of tissue may be obtained from the patient, for example through collection of a biopsy or by fine needle aspiration (FNA), and assessed for levels of IGF2BP3 fusion protein, fusion mRNA, and/or genomic events up to 65,000 bases upstream of the IGF2BP3 gene. Numerous methods may be employed to measure the amount of IGF2BP3 If, consistent with the observations presented herein, the tissue sample reflects elevated levels of IGF2BP3 fusion protein, fusion mRNA, and/or genetic evidence of fusion events upstream of IGF2BP3, then the patient would identified as a promising potential candidate for therapeutic intervention, for example, using experimentally established agents that disrupt IGF1R signaling (e.g., linsitinib, monoclonal antibodies). Such preselection of patients, as provided by the present invention, will overcome the variability of responsiveness to inhibitors of IGF1R signaling observed in clinical trials conducted to date by dramatically increasing the responsivity of the preselected patient population to IGF1R signaling intervention.

Generally, the experimentally established agents useful for treatment of cancers identified using the methods of the present invention include any compounds or biologically generated molecules that disrupt IGF1R signaling. For example, monoclonal antibodies that are targeted to IGF1R are useful within the context of the present invention and include figitumumab, cixutumumab, AMG-479, BIIB022, dalotuzumab, robatumumab, and F 50035. Further, monoclonal antibodies that are targeted to the IGF1/2 peptide ligands (e.g., Medi-573) may also be useful within the context of the present invention. Additionally, small molecule inhibitors of IGF1R signaling may also be useful within the context of the present invention and include BMS-754807, linsitinib, XL228, AXL1717, INSM-18, and NVP AEW541.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A method of detecting a thyroid adenoma associated (THADA) gene fusion thyroid cancer in a human patient, comprising the steps of:
obtaining a tissue sample from a thyroid tumor in the human patient; extracting chromosomal DNA, mRNA, or combinations thereof from the tissue sample; assaying the chromosomal DNA and/or mRNA for the presence of a genetic fusion event between THADA exons 28, 29, 30, or 36 and a breakpoint located upstream of the Insulin-like growth factor 2 binding protein 3 (IGF2BP3) gene at LOC389473 including chromosome 7 position 23,521,997; wherein the presence of the THADA-LOC389473 fusion event indicates that the human patient has a THADA gene fusion cancer; wherein the chromosome 7 position 23,521,997 is with respect to genome build 37 UCSC/genome browser version 19; and subsequently surgically removing the THADA gene fusion thyroid cancer.

2. The method of claim 1, wherein the thyroid tumor is a papillary thyroid carcinoma.

3. The method of claim 1, wherein the obtaining step is accomplished by fine needle aspiration or biopsy.

4. The method of claim 1, further comprising the steps of: extracting IGF2BP3 protein from the tissue sample; and measuring levels of the IGF2BP3 protein in the tissue sample by immunohistochemistry or Western blot analysis;

wherein elevated levels of IGF2BP3 protein compared to normal tissue indicates the presence of a cancer.

5. The method of claim 1, wherein the assaying step utilizes a method selected from the group consisting of RT-PCR, PCR, FISH, and combinations thereof.

6. A method of treating a thyroid cancer in a patient with a thyroid tumor with a therapeutic intervention, comprising the steps of:

obtaining a tissue sample from the tumor in the human patient; extracting chromosomal DNA, mRNA, or combinations thereof from the tissue sample;

assaying the chromosomal DNA and/or mRNA for the presence of a genetic fusion event between THADA exons 28, 29, 30, or 36 and a breakpoint located upstream of the Insulin-like growth factor 2 binding protein 3 (IGF2BP3) gene at LOC389473 including chromosome 7 position 23,521,997; wherein the presence of the THADA-LOC389473 fusion event indicates that the human patient has a THADA gene fusion cancer; wherein the chromosome 7 position 23,521,997 is with respect to genome build 37 UCSC/genome browser version 19; measuring IGF2BP3 protein expression in the tissue sample; and subsequently providing the patient with the therapeutic intervention if IGF2BP3 protein expression is elevated compared to normal tissue, wherein the therapeutic intervention comprises surgical removal of the tumor or administration of one or more therapeutic agents selected from a monoclonal antibody that disrupts IGF1R signaling and a small molecule inhibitor that disrupts IGF1R signaling.

7. The method of claim 6, wherein the therapeutic intervention is surgical removal of the tumor.

8. The method of claim 6, wherein the cancer comprises thyroid cancer.

9. The method of claim 8, wherein the thyroid cancer is papillary thyroid carcinoma.

10. The method of claim 6, wherein the tissue sample comprises a fine needle aspiration (FNA) tissue sample.

* * * * *